US008939885B2

(12) United States Patent
Martin

(10) Patent No.: US 8,939,885 B2
(45) Date of Patent: Jan. 27, 2015

(54) SYSTEM AND METHOD FOR ELICITING A RELAXATION RESPONSE

(76) Inventor: Penelope S. Martin, Rochester, NY (US)

( * ) Notice: Subject to any disclaimer, the term of this patent is extended or adjusted under 35 U.S.C. 154(b) by 349 days.

(21) Appl. No.: 13/235,160

(22) Filed: Sep. 16, 2011

(65) Prior Publication Data
US 2012/0071706 A1 Mar. 22, 2012

Related U.S. Application Data

(60) Provisional application No. 61/383,761, filed on Sep. 17, 2010, provisional application No. 61/534,546, filed on Sep. 14, 2011.

(51) Int. Cl.
A61M 21/00 (2006.01)
A61M 21/02 (2006.01)
G06T 7/40 (2006.01)

(52) U.S. Cl.
CPC .............. A61M 21/02 (2013.01); G06T 7/406 (2013.01); A61M 2021/005 (2013.01)
USPC ............... 600/27; 600/28; 128/897; 128/898; 128/899

(58) Field of Classification Search
USPC ................................. 600/26–28; 128/897–899
See application file for complete search history.

(56) References Cited

U.S. PATENT DOCUMENTS

| 5,054,101 A * | 10/1991 | Prakash ........................ 382/270 |
| 5,676,633 A | 10/1997 | August |
| 5,732,158 A * | 3/1998 | Jaenisch ....................... 382/249 |
| 6,102,846 A | 8/2000 | Patton et al. |
| 6,254,527 B1 | 7/2001 | August |
| 6,306,077 B1 | 10/2001 | Prabhu et al. |
| 6,396,962 B1 * | 5/2002 | Haffey et al. ................. 382/298 |
| 6,503,188 B1 | 1/2003 | August |
| 6,896,655 B2 | 5/2005 | Patton et al. |
| 7,177,079 B2 * | 2/2007 | Cromer et al. ................ 359/460 |
| 2005/0117800 A1 * | 6/2005 | Diggins ........................ 382/170 |

OTHER PUBLICATIONS

Taylor (Reduction of Physiological Stress Using Fractal Art and Architecture; Jun. 2006, vol. 39, No. 3, pp. 245-251; Posted online May 25, 2006) Listed on IDS filed by applicant on Apr. 30, 2012.*
Alzheimer's 2011 Alzheimer's Disease Facts and Figures, Alzheimer's & Dementia; Alzheimer's Association; vol. 7, Issue 2; 68 pages.
Alzheimer's Disease facts and figures 2010. The Alzheimer's Association. (2007). Retrieved Mar. 10, 2011, from alz.org/national/documents/report alzfactsfigures2010.pdf.

(Continued)

Primary Examiner — Christine Matthews
Assistant Examiner — Sunita Reddy
(74) Attorney, Agent, or Firm — Duane C. Basch; Basch & Nickerson LLP

(57) ABSTRACT

The disclosed system and method are directed to qualifying an image(s) and exposing an individual to the qualified image (s) for the purpose of eliciting a relaxation response. More specifically, a sequential rendition of qualified images are presented to either a normal or cognitively impaired person in order to elicit relaxation and/or reduce agitation. Qualified images include those with both particular natural landscape content or elements (e.g., low vegetative growth, an open area, trees, a horizon, a visible sky, an absence of any man-made structures, and fresh water) and a particular average fractal dimension.

23 Claims, 6 Drawing Sheets

(56) References Cited

OTHER PUBLICATIONS

American Geriatrics Society and American Association for Geriatric Psychiatry Expert Panel on Quality Mental Health Care in Nursing Homes. (2003). Consensus statement on improving the quality of mental health care in U.S. nursing homes: Management of depression and behavioral symptoms associated with dementia. Journal of the American Geriatrics Society, 51, 1287-1298.
Appleton, J. (1975). Behavior and environment. In the Experience of landscape (pp. 58-80). New York: John Wiley & Sons.
Artnak, K. E., & Benson, M. (2005). Evaluating HIPAA compliance: A guide for researchers, policy boards, and IRBs. Nursing Outlook, 53(2), 79-87.
Baker, K, Holloway, J., Holtkamp, C. C. C Larsson, A., Hartman, L. C., Pearce, R., et al. (2003). Effects of multi-sensory stimulation for people with dementia. Journal of Advanced Nursing, 43, 465-477.
Ballard, C. G., Margallo-Lana, M., Fossey, J., Reichelt, K., Myint, P, Potkins, D., et al. (2001). A 1-year follow-up study of behavioral and psychological symptoms in dementia among people in care environments. Journal of Clinical Psychiatry, 62, 631-636.
Ballard, C. G., O'Brien, J. T., Reichelt, K., & Perry, E. K. (2002). Aromatherapy as a safe and effective treatment for management of agitation in severe dementia: The results of a double-blind placebo-controlled trial with Melissa. Journal of Clinical Psychiatry, 63, 553-558.
Bassen, S., & Baltazar, V. (1997). Flowers, flowers everywhere: Creative horticulture programming at the Hebrew Home for the Aged at Riverdale. Geriatric Nursing, 18(2), 53-56.
Beck, C Rossby, L & Baldwin, B. (1991). Correlates of disruptive behavior in cognitively impaired elderly nursing home residents. Archives of Psychiatric Nursing, V; 281-291.
BedscapesTM Healing Environments: Research results. (2001b). Retrieved Mar. 11, 2011, from bedscapes.com/research.htm.
BedscapesTM Healing Environments: The environments. (2001a). Retrieved Mar. 11, 2011, from bedscapes.com/environments.htm.
Beers, M.H. et al. (Eds.). (2009-2010). Delirium and dementia: Behavior disorders in dementia. In The Merck manual of geriatrics (3rd ed., Section 5, Chap. 41, Part on Treatment,¶1). Whitehouse Station, NJ: Merck & Co., Inc. Retrieved Mar. 15, 2011, from merck. manuals.com/mm geriatric s/sec5/ch41. htm.
Black, B. S., Brandt, J., Rabins, P. V., Samus, Q. M Steele, C. D., Lyketsos, C. G., et al. (2008). Predictors of providing informed consent or assent for research participation in assisted living residents. American Journal of Psychiatry, 16 (1), 83-91.
Brawley, E. C. (2002). Therapeutic gardens for individuals with Alzheimer's Disease. Alzheimer's Care Quarterly, 3(1), 7-11.
Buettner, L. L. (1999). Simple pleasures: A multilevel sensorimotor intervention for nursing home residents with dementia. American Journal of Alzheimer's Disease, 14 (1), 41-52.
Callen, D. J. A., Black, S. E., & Caldwell, C. B. (2002). Limbic system perfusion in Alzheimer's disease measured by MRI-coregistered HiMPAO SPET. European Journal of Nuclear Medicine and Molecular Imaging, 29, 899-906.
Callen, D. J., Black, S. E., Gao, F., Caldwell, C. B., Szalai, J. P. (2001). Beyond the hippocampus: MRI volumetry confirms widespread limbic atrophy in AD. Neurology, 57, 1669-1674.
Camberg, L., Woods, P., Ooi, W. L., Hurley, A., Volicer, L, Ashley, J., et al. (1999). Evaluation of simulated presence: A personalized approach to enhance well-being in persons with Alzheimer's Disease [Electronic version]. Journal of the American Geriatrics Society, 47, 446-452.
Carson, S., McDonagh, M. S., & Peterson, K. (2006). A systematic review of the efficacy and safety of atypical antipsychotics in patients with psychological and behavioral symptoms of dementia. Journal of the American Geriatrics Society, 54, 354-361.
Chandler, J. D., & Chandler, J. E. (1988). The prevalence of neuropsychiatric disorders in a nursing home population. Journal of Geriatric Psychiatry and Neurology, 1(2), 71-76.
Chang, C.-Y, & Perng, J.-L. (1998). Effect of landscape on psychological and physical responses. Journal of Therapeutic Horticulture, IX, 73-76.
Cohen-Mansfield, J. (1986). Agitated behaviors in the elderly II: Preliminary results in the cognitively deteriorated. Journal of the American Geriatrics Society, 34, 722-727.
Cohen-Mansfield, J. 1988). Agitated behavior and cognitive functioning in nursing home residents: Preliminary results. Clinical Gerontologist, 7(314), 11-22.
Cohen-Mansfield, J. 1995). Assessment of disruptive behavior/agitation in the elderly: Function, methods, and difficulties. Journal of Geriatric Psychiatry and Neurology, 8(1), 52-60.
Cohen-Mansfield, J. & Billig, N. (1986). Agitated behaviors in the elderly I: A conceptual review. Journal of the American Geriatrics Society, 34, 711-721.
Cohen-Mansfield, J. Libin, A. (2004). Assessment of agitation in elderly patients with dementia: Correlations between informant rating and direct observation.International Journal of Geriatric Psychiatry, 19, 881-891.
Cohen-Mansfield, J. Marx, M. S., & Rosenthal, A. S. (1989). A description of agitation in a nursing home. Journal of Gerontology, 44(3), M77-M84.
Cohen-Mansfield, J. Marx, M. S., & Werner, P. (1992). Agitation in elderly persons: An integrative report of findings in a nursing home. International Psychogeriatrics, 4(Supp. 2), 221-240.
Cohen-Mansfield, J.; Werner, P. (1998). The effects of an enhanced enviroment on nursing home residents who pace. The Gerontologist, 38, 199-208.
Cox, H., Burns, I., & Savage, S. (2004). Multisensory environments for leisure: Promoting well-being in nursing home residents with dementia. Journal of Gerontological Nursing, 30(2), 37-45.
Coyne, A. C., Reichman, W. E., & Berbig, L. J. (1993). The relationship between dementia and elder abuse. American Journal of Psychiatry, 150, 643-646.
Desai, A. K., & Grossberg, G. T. (2001). Recognition and management of behavioral disturbances in dementia. Primary Care Companion—Journal of Clinical Psychiatry, 3(3), 93-109.
Detweiler, M.; Anderson, M. S. (2002). Wander gardens: Expanding the dementia treatment environment. Annals of Long-Term Care, 10(3), 68-74.
Devanand, D. P., Brockington, C. D., Moody, B. J., Brown, R. P., Mayeux, R., Endicott, J., et al. (1992). Behavioral syndromes in Alzheimer's Disease. International Psychogeriatrics, -I (Supp2), 161-184.
Deyoung, S., Just, G., & Harrison, R. (2002). Decreasing aggressive, agitated, or disruptive behavior: Participation in a behavior management unit. Journal of Gerontological Nursing, 28(6), 22-31.
Diette, G. B., Lechtzin, N., Haponik, E., Devrotes, A., & Rubin, H. R. (2003). Distraction therapy with nature sights and sounds reduces pain during flexible bronchoscopy: A complementary approach to routine analgesia. Chest, 123, 941-948.
Eden Alternative (2009). Our 10 principles. Retrieved Mar. 10, 2011, from edenalt.orgiour-10-priciples.
Evans, G. W., & Cohen, S. (1987). Environmental stress. In D. Stokols & I. Altman (Eds.), Handbook of environmental psychology (pp. 571-610). New York: John Wiley.
Everitt, D. E., Fields, D. R., Soumerai, S. S., & Avorn, J. (1991). Resident behavior and staff distress in the nursing home. Journal of the American Geriatrics Society, 39, 792-798.
Federal Interagency Forum on Aging-Related Statistics. (2010). Older Americans 2010: Key indicators of well-being. Washington, D. C.: U. S. Government Printing Office.
Finkel, S. I., Lyons, J. S., & Anderson, R. L. (1993). A brief agitation rating scale (BARS) for nursing home elderly. Journal of the American Geriatrics Society, 41, 50-52.
Folstein, M. F., Folstein, S. E., & McHugh, P. R. (1975). "Mini-mental state:" A practical method for grading the cognitive state of patients for the clinician. Journal of Psychiatric Research, 12, 189-198.
Forsythe, A., Nadal, M., Sheehy, N., Cela-Conde, C. J. and Sawey, M. (2011), Predicting beauty: Fractal dimension and visual complexity in art. British Journal of Psychology, 102: 49-70. doi: 10.1348/000712610X498958.

(56) References Cited

OTHER PUBLICATIONS

Garland, K Beer, E., Eppingstall, B., & O'Connor, D. W. (2007). A comparison of two treatments of agitated behavior in nursing home residents with dementia: Simulated family presence and preferred music. American Journal of Geriatric Psychiatry, 15, 514-521.

Gegenftwtner, K. R., & Rieger, J. (2000). Sensory and cognitive contributions of color to the recognition of natural scenes. Current Biology, 10, 805-808.

Gerdner, L. A. (2000). Effects of individualized versus classical "relaxation" music on the frequency of agitation in elderly persons with Alzheimer's disease and related disorders. International Psychogeriatrics, 12 (1), 49-65.

Gerdner, L. A., Buckwalter, K. C., & Hall, G. R. (2005). Temporal patterning of agitation and stressors associated with agitation: Case profiles to illustrate the Progressively Lowered Stress Threshold Model. The Journal of the American Psychiatric Nurses Association, 11, 215-222.

Greene, J., Asp, J., & Crane, N. (1985). Specialized management of the Alzheimer's patient: Does it make a difference? Journal of the Tennessee Medical Association, 78(9), 58-63.

Hall, G. R., & Buckwalter, K. C. (1987). Progressively lowered stress threshold: A conceptual model for care of adults with Alzheimer's Disease. Archives of Psychiatric Nursing, 1, 399-406.

HarFA (Harmonic and Fractal Image Analyzer) , 2 webpages downloaded Aug. 17, 2011; fch.vutbr.cz/lectures/imagesci/includs/harfa_introduction.inc.php.

Hartmaier, S. L. et al. (1995). Validation of the Minimum Data Set Cognitive Performance Scale: Agreement with the Mini-Mental State Examination. Journal of Gerontology: Medical Sciences, 50A, M128-M133.

Health Care Financing Administration, Department of Health and Human Services. (2002) Omnibus Budget Reconciliation Act of 1987, 42 C.F.R. § 483.13 (GPO Access stock No. 869-060-00176-0).

Heerwagen, J. H. (1990). The psychological aspects of windows and window design. In K. H. Anthony, J. Choi, & B. Orland, (Eds.), Coming of age:EDR,421/1990: Proceedings of the twenty first animal conference of the Environmental Design Research Association (pp. 269-280). Oklahoma City, OK: Environmental Design Research Association.

Heerwagen, J. H., & Orians, G. H. (1993). Humans, habitats, and aesthetics—Flowers as resource signals. In S. R. Kellen & E. 0. Wilson (Eds.), The biophilia hypothesis (p. 163) Washington, DC: Island Press.

Hemi-Sync / Brain Sync—Alpha Waves with Fractal Imagery for Relaxation and Creative Visualization; 3 webpages downloaded Sep. 13, 2011.

Hertzog, T., Herbert, E., Kaplan, R., & Crooks, C. (2000). Cultural and developmental comparisons of landscape perceptions and preferences. Environment and Behavior, 32, 323-346.

Holmes, D., Teresi, J., Weiner, A., Monaco, C., Ronch, J., & Vickers, R. (1990) Impacts associated with special care units in long-term care facilities. The Gerontologist, 30, 178-183.

Hoogendijk, W. J., Meynen, G., Endert, E., Hofman, M. A., & Swaab, D. F. (2006). Increased cerebrospinal fluid cortisol level in Alzheimer's disease is not related to depression. Neurobiology of Aging, 27, 780.e1-780.e2.

Hsieh, H. F., & Wang, J.J. (2003). Effect of reminiscence therapy on depression in older adults: A systematic review. International Journal of Nursing Studies, 40, 335-345.

Hurley, A. C., Volicer, L., Camberg, L., Ashley, J., Woods, P., Odenheimer, G., et al. (1999). Measurement of observed agitation in patients with dementia of the Alzheimer type. Journal of Mental Health and Aging, 5(2), 117-133.

International Psychogeriatric Association (IPA). (2002). BPSD: Behavioral and psychological symptoms of dementia educational pack (Rev.).

Jendreski, M., Truglio-Londrigan, M., Kole, H., & Cunningham, D. (2007). Hallway Video Enhancement Project: An innovative practice strategy. Activities Directors' Quarterly for Alzheimer's & Other Dementia Patients, 8 (1), 7-12.

Jennings, B., & Vance, D. (2002). The short-term effects of music therapy on different types of agitation in adults with Alzheimer's. Activities, Adaptation, & Aging, 26 (4), 27-33.

Joint Commission Resources, Inc. (2004). The risk manager and patient safety: Fall prevention. In preview of Accreditation issues for risk managers (pp. 17-50). Oakbrook Terrace.

Kaplan, S. (1978). Attention and fascination: The search for cognitive clarity. In R. Kaplan & S. Kaplan (Eds.), Humanscape: Environments for people (pp. 84-90). North Scituate, MA: Duxbury Press.

Keller. H. H., Gibbs, A. J., Goy, R. E., Patillo, M. S., & Brown, H. M. (2003). Prevention of weight loss in dementia with comprehensive nutritional treatment. Journal of the American Geriatric Society, 51, 945-951.

Kim, E, & Mattson, R. H. (2002). Stress recovery effects of viewing red-flowering geraniums. Journal of Therapeutic Horticulture, MI, 4-12.

Kong, E. H. (2005). Agitation in dementia: Concept clarification. Journal of Advanced Nursing, 52, 526-536.

Kovach, C., & Stearns, S. (1994). DSCUs: A study of behavior before and after residence. Journal of Gerontological Nursing, 20(12), 33-41.

Lane, D. (2004). Hyperstat online: An introductory statistics textbook and online tutorial for help in statistics courses: Power: Variance. 2 webpages.

Lee, H. B., Harmer, J. A., Yokley, J. L., Appleby, B, Hurowitz, L., & Lyketsos, C. G. (2007). Clozapine for treatment-resistant agitation in dementia. Journal of Geriatric Psychiatry, and Neurology, 20, 178-182.

Lin, Y. C Dai, Y. T., & Hwang, S. L. (2003). The effect of reminiscence on the elderly population: A systematic review. Public Health Nursing, 20, 297-306.

Lund, D. A., Hill, R. D., Caserta, M. S., & Wright, S. D. (1995). Video Respite': An innovative resource for family, professional caregivers, and persons with dementia. The Gerontologist, 35, 683-687.

Maas, M., Swanson, E Specht, J., & Buckwalter, K. (1994). Alzheimer's special care units. Nursing Clinics of North America, 29, 173-194.

Magri, F., Cravello, L., Barili, L., Sarra, S., Cinchetti, W Salmoiraghi, F., et al. (2006). Stress and dementia: The role of the hypothalamic-pituitary-adrenal axis. Aging Clinical and Experimental Research, 18, 167-170.

Martin, P.S.; A Cross-Over Study to Investigate the Use of Natural Landscape Photographs with Particular Content and Pattern to Reduce Agitation in Nursing Home Residents with Alzheimer's Dementia; Apr. 25, 2011; 199 pages.

Marx, M. S., Cohen-Mansfield, J., & Werner, P. (1990). Agitation and falls in institutionalized elderly persons. Journal of Applied Gerontology, 9(1), 106-117.

McGonigal-Kenney, M. L., & Schutte, D. L., With S. Adams, & M. G. Titler (Eds.).(2006). Evidence-based guideline: Nonpharmacological management of agitated behaviors in persons with Alzheimer's Disease and other chronic dementing conditions. Journal of Geriatric Nursing, 32(2), 9-14.

Miller, A. C., Hickman, L.C., & Lemasters, G. K. (1992). A distraction technique for control of burn pain. Journal of Burn Care & Rehabilitation, 13, 576-580.

Miller, S., Vermeersch, P. E. H., Bohan, K., Renbarger, K., Kruep, A, & Sacre, S. (2001). Audio presence intervention for decreasing agitation in people with dementia. Geriatric Nursing, 22(2), 66-70.

Mooney, P, & Nicell, P. L. (1992). The importance of exterior environment for Alzheimer residents: Effective care and risk management. Healthcare Management Forum, 5(2), 23-29.

Moore, E. 0. (1981). A prison environment's effect on health care service demands. Journal of Environmental Systems, 11(1), 17-34.

Morris, J. N., Fries, B. E., Mehr, D. R., Hawes, C., Phillips, C., Mor, V., et al. (1994). MDS cognitive performance scale. Journal of Gerontology: Medical Sciences, 49, M174-M182.

Nanda, U., Eisen, S., Baladandayuthapani, V. (2008). Undertaking an art survey to compare patient versus student art preferences. Environment and Behavior, -ID, 269-301.

Nasr, S. Z., & Osterweil, D. (1999). The nonpharmacologic management of agitation in the nursing home: A consensus approach. Annals of Long-Term Care, 7, 171-180.

(56) References Cited

OTHER PUBLICATIONS

Nowak, L., & Davis, J. E. (2007). A qualitative examination of the phenomenon of sundowning. Journal of Nursing Scholarship, 39, 256-258.

Orians, G. H. (1986). An ecological and evolutionary approach to landscape aesthetics. In E. C. Penning-Rowsell & D. I. Lowenthal (Eds.), Landscape meaning and values (pp. 3-25). London: Allen and Unwin.

Orians, G. H., & Heerwagen, J. H. (1992). Evolved responses to landscape. In J. Barckow, L. Cosmides, & J. Tooby (eds.), Adapted mind: Evolutionary psychology and the generation of culture (pp. 555-580). Oxford, U. K.: Oxford University Press.

Orians, G.H. (1980). Habitat selection: General theory and application to human behavior. In J. S. Lockard (Ed.), The evolution of human social behavior (pp. 49-66). Chicago: Elsevier.

Pachana, N. A., McWha, L., & Arathoon, M. (2003). Passive therapeutic gardens: A study on an inpatient geriatric ward. Journal of Gerontological Nursing, 29(5), 4-10.

Parsons, R., Tassinary, L. G., Ulrich, R. S., Hebl, M. R., & Grossman-Alexander, M. (1998). The view from the road: Implications for stress recovery and immunization. Journal of Environmental Psychology, 18(2), 113-13.

Plassman, B. L., Langa, K. M., Fisher, G. G., Heeringa, S. G., Weir, D. R., Ofstedal, M. B., et al. (2007). Prevalence of dementia in the United States: The aging, demographics, and memory study. Neuroepidemiology, 29, 125-132.

Profenno, L. A., & Tariot, P. N. (2004). Pharmacologic management of agitation in Alzheimer's Disease. Dementia and Geriatric Cognitive Disorders, 17, 65-77.

Reisberg, B., Borenstein, J., Salob, S. P., Ferris, S. H., Franssen, E., & Georgotas, A. (1987). Behavioral symptoms in Alzheimer's Disease: Phenomenology and treatment. Journal of Clinical Psychiatry, 48 (Supp.), 9-15.

Rhoades, J. A., & Krauss, N. A. for the Agency for Healthcare Research and Quality, Rockville, MD. (Mar. 2004). Chartbook #3: Nursing home trends, 1987 to 1996.

Robb, S. S., Boyd, M., & Pristash, C. L. (1980). A wine bottle, plant, and puppy: Catalysts for social behavior. Journal of Gerontological Nursing, 12, 721-728.

Rovner, B. W., Kafonek, S., Filipp, L., Lucas, M. J., & Folstein, M. F. (1986). Prevalence of mental illness in a community nursing home. American Journal of Psychiatry, 143, 1446-1449.

Satlin, A., Volicer, L., Ross, V., Hertz, L., & Campbell, S. (1992). Bright light treatment for behavioral and sleep disturbances in inpatients with Alzheimer's disease. American Journal of Psychiatry, 149, 1028-1032.

Schneider, L. S., Dagerman, K., & Insel, P. S. (2006). Efficacy and adverse effects of atypical antipsychotics for dementia: Meta-analysis of randomized, placebo-controlled trials. American Journal of Geriatric Psychiatry, 14, 191-210.

Schoenfeld, David A. (2008). Find statistical considerations for a cross-over study where the outcome is a measurement. In John C. Pezzullo home page: Interactive statistics pages. Retrieved Jul. 23, 2008, from statpages.org.

Selye, H. (1946). The general adaptation syndrome and the diseases of adaptation. The Journal of Clinical Endocrinology, 6, 117-231.

Selye, H. (1976a).The birth of the G.A.S.: The first publication on the stress syndrome. A word about discovery. The search for a name. In the stress of life (Rev. ed., pp. 29-54). New York: McGraw-Hill.

Selye, H. (1976b). Dissecting a biologic mechanism: Interrelations in the endocrine system. Basic mechanisms of stress reactions. The essence of the stress response. In the stress of life (Rev. ed., pp. 97-127). New York: McGraw-Hill.

Shah, A., Evans, H., & Parkash, N. (1998). Evaluation of three aggression/agitation behaviour rating scales for use on an acute admission and assessment psychogeriatric ward. International Journal of Geriatric Psychiatry, 13, 415-420.

Sloane, P. D., Mitchell, C. M., Preisser, J. S., Phillips, C., Commander, C., & Burke, E. (1998). Environmental correlates of resident agitation in Alzheimer's Disease special care units. Journal of the American Geriatrics Society, 46, 862-869.

Sloane, P. D., Zimmerman, S., Gruber-Baldini, A. L., Hebel, J. R., Magaziner, J., & Konrad, T. R. (2005). Health and functional outcomes and health care utilization of persons with dementia in residential care and assisted living facilities: Comparison with nursing homes. The Gerontologist, 45 (Special Issue 1), 124-132.

Snyder, M Egan, E.C., & Burns, K. R. (1995a). Efficacy of hand massage in decreasing agitation behaviors associated with care activities in persons with dementia. Geriatric Nursing, 16(2), 60-63.

Snyder, M., Egan, E.C., & Burns, K. R. (1995b). Interventions for decreasing agitation behaviors in persons with dementia. Journal of Gerontological Nursing, 21(7), 34-40.

Souder, E., & O'Sullivan, P. (2003). Disruptive behaviors of older adults in an institutional setting: Staff time required to manage disruptions. Journal of Gerontological Nursing, 29(8), 31-36.

Souder, E., Heithoff, K O'Sullivan, P. S., Lancaster, A. E., & Beck, C. (1999). Identifying patterns of disruptive behavior in long-term care residents [Electronic version]. Journal of the American Geriatrics Society, 47, 830-836.

Special Committee on Aging, United States Senate. (May 2004). Developments in aging: 2001 and 2002, REPT. 108-265, vol. 1 [Electronic version]. Washington, DC: U.S. Government Printing Office.

Swaab, D. F., Bao, A. M., & Lucassen, P. J. (2005). The stress system in the human brain in depression and neurodegeneration. Aging Research Reviews, 4, 141-194. 14.3.

Taylor, R. P., Spehar, B Wise, J. A., Clifford, C. W. G Newell, B. R., Hagerhall, C. M., et al. (2005). Perceptual and physiological responses to the visual complexity of fractal patterns. Journal of Non-Linear Dynamics, Psychology, and Life Sciences, 9(1), 89-114.

Taylor, R.P.; Reduction of Physiological Stress Using Fractal Art and Architecture; Jun. 2006, vol. 39, No. 3, pp. 245-251; Posted Online May 25, 2006. (doi:10.1162/leon.2006.39.3.245) © 2006 Massachusetts Institute of Technology.

Testad, I., Aasland, A. M., & Aarsland, D. (2005). The effect of staff training on the use of restraint in dementia: a single-blind randomized controlled trial. International Journal of Geriatric Psychiatry, 20, 587-590.

Thomas, W., & Johansson, C. (2003). Elderhood in Eden. Topics in Geriatric Rehabilitation, 19, 282-290.

Tse, M. M. Y., Ng, J. K. F., Chung, J. W. Y., & Wong, T. K. S. (2002). The effect of visual stimuli on pain threshold and tolerance. Journal of Clinical Nursing,I I , 462-469.

Tyson, M. M. (2002). Treatment gardens: Naturally mapped environments and independence. Alzheimer's Care Quarterly, 3(1), 55-60.

Ulrich, R.S. (1979). Visual landscapes and psychological well-being. Landscape Research, 4(1), 17-23.

Ulrich, R.S (1981). Natural versus urban scenes: Some psychophysiological effects. Environment and Behavior, 13, 523-556.

Ulrich, R.S. (1983). Aesthetic and affective response to natural environment. In I. Altman & J. F. Wohlwill (Eds.), Behavior and the natural environment (vol. 6, pp. 85-125). New York: Plenum Press.

Ulrich, R.S. (1984). View through a window may influence recovery from surgery. Science, 224, 420-421.

Ulrich, R.S. (1993). Biophilia, biophobia, and natural landscapes. In S. R. Kellen & E. 0. Wilson (Eds.), The biophilia hypothesis (pp. 73-137). Washington, DC: Island Press.

Ulrich, R.S. Ulrich, R. S. (1997). Pre-symposium workshop: A theory of supportive design for healthcare facilities. Journal of Healthcare Design: Proceedings from the Symposium on Healthcare Design, 9, 3-7.

Ulrich, R.S. Lunden, 0., & Eltinge, J. L. (1993). Effects of exposure to nature and abstract pictures on patients recovering from open heart surgery [Abstract]. Psychophysiology: Journal of the Society for Psychophysiological Research, 30(Suppl. 1), S7.

Ulrich, R.S. & Parsons, R. (1992). Influences of passive experiences with plants on individual well-being and health. In D. Reif (Ed.), The role of horticulture in human well-being and social development: A national symposium (pp. 93-105). Portland, OR: Timber Press.

Ulrich, R.S. ; Simons, R. F., Losito, B. D., Fiorito, E., Miles, M. A., & Zelson, M. (1991). Stress recovery during exposure to natural and urban environments. Journal of Environmental Psychology, 11, 201-230.

(56) References Cited

OTHER PUBLICATIONS

University of Rochester Medical Center, Research Subjects Review Board (2006). Guidance for investigators. Retrieved Jul. 31, 2008, from Web site: urmc.rochester.edu/rsrb/ leading to urmc.rochester.eduksrb/pdVinvguidance.pdf.

Van Tonder, G. J., Lyons, M. J., and Ejima, Y. (2002). Visual structure of a Japanese Zen garden: The mysterious appeal of a simple and ancient composition of rocks is unveiled. Nature, 419, 359-360.

Van Weert, J. C. M., Van Dulmen, A. M Spreeuwenberg, P. M. M., Ribbe, M. W., & Bensing, J. M. (2005). Behavioral and mood effects of Snoezelen integrated into 24-hour dementia care. Journal of the American Geriatrics Society, , 24-3353.

Verderber, S. (1986). Dimensions of person-window transactions in the hospital environment. Environment and Behavior, 18, 450-466.

Volicer, L., Bass, E. A., & Luther, S. L. (2007). Agitation and resistiveness to care are two separate behavioral syndromes of dementia. Journal of the American Medical Directors Association, 8, 527-532.

Volicer, L., Camberg, L., Hurley, A. C., Ashley, J., Woods, P., Ooi, W. L., et al. (1999). Dimensions of decreased psychological well-being in advanced dementia. Alzheimer's Disease and Associated Disorders, 13, 192-20.

Voyer, P., Verreault, R., Mengue, P. M., Laurin, D. Rochette, L., Martin, L. S., et al. (2005). Determinants of neuroleptic drug use in long-term facilities for elderly persons. The Journal of Applied Gerontology, 24(3), 179-195.

Walsh, J. S., Welch, H., & Larson, E. B. (1990). Survival of Outpatients with Alzheimer-type dementia. Annals of Internal Medicine, 113, 429-434.

Wang, K. L., & Hermann, C. (2006). Pilot study to test the effectiveness of Healing Touch on agitation in people with dementia. Geriatric Nursing, 27(1), 34-40.

Watson, N. M Wells, T. J., & Cox, C. (1998). Rocking chair therapy for dementia patients: Its effect on psychosocial well-being and balance. American Journal of Alzheimer's Disease, 13, 296-308.

Weiner, P. K., Kiosses, D. N., Klimstra, S., Murphy, C., & Alexopoulos, G. S. (2001). A short-term inpatient program for agitated demented nursing home residents. International Journal of Geriatric Psychiatry, 16, 866-872.

Whall, A. L., Black, M. E., Groh, C. J., Yankou, D. J., Kupferschmid, B. J., & Foster, N. L. (1997). The effect of natural environments upon agitation and aggression in late stage dementia patients. American Journal of Alzheimer's Disease, 12, 216-220.

Whall, A., Gillis, G, L., Yankou, D Booth, D. E., & Beel-Bates, C. A. (1992). Disruptive behavior in elderly nursing home residents: A survey of nursing staff. Journal of Gerontological Nursing, 18(10), 13-17.

Wilson, E. 0. (1993). Biophilia and the conservation ethic. In S. R. Kellert & E. 0. Wilson (Eds.), The biophilia hypothesis (pp. 31-41). Washington, DC: Island Press.

Winger, J., Schirm, V., & Stewart, D. (1987). Aggressive behavior in long-term care. Journal of Psychosocial Nursing, 25(4), 28-33.

Wise, J. A., & Rosenberg, E. (1988). The effects of interior treatments on performance stress in three types of mental tasks. Center for Integrated Facilities Research (CIFR) Technical Report No. 002-02-1988. Sunnyvale, CA: NASA-ARC.

Wise, J. A., & Taylor, R. P. (2002). Fractal design strategies for enhancement of knowledge work environments. Bridging Fundamentals & New Opportunities: FIFES 46th Annual Meeting, Sep.-Oct. 2002, Baltimore, MD (pp. 854-858). Santa Monica, CA: The Human Factors and Ergonomics Society.

Wohlwill, J. F. (1983). The concept of nature: A psychologist's view. In I. Altman & J. F. Wohlwill (Eds.), Behavior and the natural environment (pp. 5-37). New York: Plenum.

Woods, D. L., & Dimond, M. (2002). The effect of Therapeutic Touch on agitated behavior and cortisol in persons with Alzheimer's Disease. Biological Research for Nursing, 4(2), 104-114.

Woods, D. L., Craven, R. F., & Whitney, J. (2005). The effect of Therapeutic Touch on behavioral symptoms of persons with dementia. Alternative Therapies in Health and Medicine, 11(1), 66-74.

Yang, M-H, Wu, S-C, Lin, J-G, & Lin, L-C. (2007). The efficacy of acupressure for decreasing agitated behaviour in dementia: A pilot study. Journal of Clinical Nursing, 16, 308-315.

Zimmer, J. G., Watson, N., & Treat, A. (1984). Behavioral problems among patients in skilled nursing facilities. American Journal of Public Health, 74, 1118-1121.

\* cited by examiner

SYSTEM AND METHOD FOR ELICITING A RELAXATION RESPONSE

This application claims priority from U.S. Provisional Patent Application 61/383,761 for "METHODS FOR ELICITING A RELAXATION RESPONSE AND DEVICES THEREOF," filed Sep. 17, 2010 by P. Martin, and U.S. Provisional Patent Application 61/534,546 for "SYSTEM AND METHOD FOR ELICITING A RELAXATION RESPONSE" filed Sep. 14, 2011 by P. Martin, both of which are hereby incorporated by reference in their entirety.

The disclosed systems and methods are directed to providing a visual experience for a person using qualified images from nature for the purpose of eliciting a relaxation response. More specifically, a sequential display of qualified images (e.g., digital images and/or video) may be presented on a relaxation display unit to elicit a physiological and psychological relaxation response, and in certain situations reduce or eliminate agitation.

BACKGROUND AND SUMMARY

Stressors are "aversive agents," including situations that are taxing or threatening (Evans & Cohen, 1987, p. 575) and lead to stress and the reactions to it. Selye, from whom the current ideas about "stress" originated, defined the concept of human stress as "the nonspecific response of the body to demands" (Selye, 1976c, p. 1) and associated it with psychological responses and multiple organ system physiological responses that may affect mental and physical health (Selye, 1946; Selye, 1976c). The totality of these adaptive reactions and the changes they produce in the human body ("the stress syndrome . . . general adaptation syndrome (G.A.S.)," Selye, 1976c, p. 1) are the subject of much attention because of the significance of the syndrome to health and health costs. The neuroendocrine responses to stress affect the human system as a whole and can impact every major organ, as well as more generalized inflammatory or infectious conditions that target multiple areas of the body (Benson & Klipper, 1975; Selye, 1976c). To name a few of the more significant issues, the stress syndrome can exacerbate heart disease, diabetes, eating and weight issues, mental health, and possibly even the growth of cancer, thereby making the treatment of these afflictions more complicated and more costly to individuals, their caregivers, and their society. To reduce this extremely pervasive stress reaction is to effect positive change in both individuals and health systems everywhere.

One means by which to address the stress reaction is with natural landscape images. Visual stimuli, as a primary sensory input processed in the brain, may provoke either positive or negative physiological responses and/or self-reported psychological states. In some cases, for example, the viewing of a complicated and unrecognizable picture, such as a piece of abstract art, challenges the mind to essentially decode the picture in creative terms in order to interpret the image, provoking an anxious state. On the other hand, certain types of images, such as images of natural landscape scenes, may elicit a physiological and/or psychological relaxation response, particularly when such images have specific characteristics as further described herein.

This has been discussed by theorists and documented in laboratory and clinical studies. Viewing photographic natural landscape scenes has been shown to reduce physiological and psychological indicators of stress in several laboratory studies with healthy young adults (Chang & Perng, 1998; Parsons, Tassinary, Ulrich, Hebl, & Grossman-Alexander, 1998; Tse, Ng, Chung, & Wong, 2002; Ulrich, 1979; Ulrich, 1981; Ulrich et al., 1991; Wise & Rosenberg, 1988). Clinical studies have demonstrated effects on pain perception, on anxiety about procedures, and on call for "as needed" medications (Diette, Lechtzin, Haponik, Devrotes, & Rubin, 2003; Heerwagen, 1990; Miller, Hickman, & Lemasters, 1992, Nanda, Eisen, Zadeh, & Owen, 2010; Ulrich, Lunden, & Eltinge, 1993; Whall et al., 1997).

The human brain, theorists say, adapted to best appreciate natural configurations that appear to favor survival and well-being (Appleton, 1975; Orians, 1980; Orians, 1986; Orians & Heerwagen, 1992; Wilson, 1993; Wohlwill, 1983). Wohlwill suggested that the human brain and senses developed in natural environments and, therefore, have an easier time processing information from such environments, being relatively fatigued by information from the historically very recent alternative constructed environments.

Evolutionary theory about human relationship to landscape has expanded to include not only the idea that humans have been genetically steered to favor natural content over man-made structures and objects, but also to encompass the idea that humans are inclined to respond to certain types of landscape most positively. Many researchers have demonstrated this (Chang & Perng, 1998; Parsons, Tassinary, Ulrich, Hebl, & Grossman-Alexander, 1998; Ulrich, 1979; Ulrich, 1981; Ulrich et al., 1991): Savannah-like (park-like) settings, especially with fresh, calm waters included, are favored over other types of scenes cross-culturally (Ulrich, 1993), as seen with American, British, Canadian, Chinese, Swedish, and Ugandan (Ulrich, 1983), as well as Australian (Hertzog, Herbert, Kaplan, & Crooks, 2000) research participants. An ongoing series of survey studies spanning several years was begun to investigate "most liked" and "least liked" features of pictures in as many countries across the globe as would participate (Wypijewski, 1997). To date, this research has demonstrated that a park-like setting with blues, greens, and fresh water is the most favorite type of scene, while linear abstract is the least favorite. This has held true universally to date, including Asian, Middle Eastern, East African, European (eastern and western), and North American samplings.

Ulrich (1993) proposed that security and "restoration" (recovery from stress response; p. 88) are the subjective qualities identified with evolutionary advantage (survival and health) that underlie the objective elements in the preferred settings—low growth mixed with trees, flat areas through which to move, horizon, and water to drink. Flowers may also be part of a preferred setting because of their evolutionary association with food resources (Heerwagen & Orians, 1993; Kim & Mattson, 2002).

Kaplan (1978) contributed to the development of thought on the basis for human response to natural landscapes by providing a more specific idea about the cognitive mechanism through which viewing natural settings might work to reduce stress and provide a restorative experience. He distinguished "voluntary attention," or attention requiring effort, from "involuntary attention," or attention requiring no effort (p. 85). According to Kaplan, voluntary attention (to time schedules, to behavior, to conversation, to health care regimens, to environmental and social cues, to tasks, etc.) requires internal suppression of distraction and creates mental fatigue. Resting this overworked cognitive state may be achieved by having attention be taken up involuntarily—by environments or environmental images that are innately interesting and that fascinate without conscious effort. Kaplan also incorporated evolutionary predisposition into his explanation at this point. From evolutionary theory, he concluded that certain images evoke involuntary attention as a survival mechanism. These images include "green things . . . gardens . . . patterns of natural vegetation . . . water" (p. 88) and are "innately fascinating, . . . attention [to them] requir[ing] no effort," (p. 86) as "survival may well have depended upon paying immediate attention to stimuli of this kind" (p. 86). This sort of attention would be instinctual and immediate, not consciously directed (Ulrich, 1983). Kaplan's premise is that attending to natural settings, or images of them, dispenses with conscious effort, and thereby reduces stress, and leads to survival advantages associated with psychological rest. From such reflections on cognitive states, stress, and restorative requirements came the idea that viewing select natural settings (innately associated with stress-reducing factors of safety, rest, and satisfaction of hunger and thirst) may counteract the stress reaction and provide some health benefit to people in stressful situations (Ulrich & Parsons, 1992).

What has thus far been overlooked in the interventions and products based on these theories and studies rooted solely in "biophilia" (Wilson, 1993—the idea that humans have an innate attraction to living things, a predisposition to focus on and respond to scenes of natural content) is the importance of pattern to human recognition of these restorative scenes. A study at NASA began to elucidate this factor. The human brain seems to be partial to certain patterns of natural landscape more than others.

We do know that many natural scenes are fractal—having patterns of shape that recur on finer and finer scales throughout the visual frame (Taylor et al., 2005). A fractal dimension may be calculated for photographic images and will range between 1.0 (a line) to 2.0 (a plane) on a logarithmic scale (Wise & Taylor, 2002). This range represents a progression in complexity, for example, an image of fluffy clouds might have a fractal dimension of 1.3, while a briar patch might have a fractal dimension of 1.8 (Wise & Taylor). Wise and Taylor hypothesized that the calming effect of natural landscape images might have to do with brain neurocircuitry evolutionarily programmed to recognize a fractal range in these scenes that corresponds to the fractal range of environments in which humans developed as a species.

Wise and Rosenberg (1988) noted, "Although certain types of trees, foliage and landforms may be highly preferred or particularly evocative, this does not imply that the active agent is in the thing itself rather than in what the thing displays" (p. 11). This idea was demonstrated by VonTonder, Lyons, and Ejima (2002). These investigators mathematically analyzed a Japanese meditation garden renowned for its meditative and relaxing character and found that, although the objects in the visual field they examined are rocks, what is seen may actually be pattern, not individual features. These rocks make the shape of a tree with extended limbs when geometric functions are applied to their positioning. VonTonder, Lyons, and Ejima suggested the brain may interpret and respond to "tree" rather than "rocks" when viewing such a scene.

In a head-to-head comparison of the stress-reducing effect of two different natural landscape scenes (Wise & Rosenberg, 1988), the one having a fractal dimension comparable to the range in the African savannah (1.3-1.5; Wise & Taylor) was the more effective at reducing a physiological manifestation of stress response (skin conductance). Kaplan mentioned the significance of pattern and stated, "An individual's likelihood of survival would be enhanced if certain kinds of patterns . . . were innately fascinating, if attention [to them] required no effort" (p. 86). With their finding about pattern, quantified as fractal dimension, Wise and Taylor demonstrated mathematically what the earlier theorists and researchers had proposed intuitively.

Reaction to pattern (fractal dimension) as part of an evolutionarily adaptive approach-avoidance response would occur at the lower levels of brain function, the limbic system (Wise & Rosenberg, 1988; Ulrich, 1983) and would, therefore, be expected to occur quickly (without conscious thought) and would not be limited by ethnicity, age, gender, or geographic location, as seems to be the case across various studies (cited above). These findings support the idea of the new intervention—evidence-based landscape images (i.e. having specific content as specified above) further qualified by mid-range fractal character—that can affect manifestations of stress in the general human population.

The study titled, "Use of Natural Landscape Photographs with Particular Content and Pattern to Reduce Agitation in Nursing Home Residents with Alzheimer's Dementia" by P. Martin, Applicant (University of Rochester, Rochester N.Y.; see U.S. Provisional Application 61/534,546), which is also hereby incorporated by reference in its entirety, tested this new intervention idea as a nonpharmacological approach to reduce agitation in elders, thought to be brought on by stress reaction. Although aspects of the disclosed embodiments may be described relative to reducing agitation in a nursing home setting, it will be appreciated that the disclosed methods and systems are equally applicable to humans in the general population. The use of natural landscape scenes does not necessitate individualized equipment, space for interaction, supervision, training, or learning and recall by the user. In fact, such use may not even require an awareness or voluntary attention. The use of natural landscape scenes with particular content and pattern is, therefore, easy and accessible, making it a potentially valuable non-pharmacologic tool for addressing stress and its many negative sequelae.

As a general rule, not just any picture of a landscape or seascape will have a desired or optimized effect of evoking a relaxation response. Rather, as has been described herein, a specific combination of image content and average fractal dimension are used to determine or identify images that are qualified to evoke desired responses, meaning they will elicit a relaxation response in the general population. These characteristics are essential for a picture or image to evoke a positive psychophysiological response. The recognition and quantification of recurring patterns within an image (including a characteristic represented by an average fractal dimension for an image) as an ingredient for imagery to be maximally calming and satisfying has yet to be applied in conjunction with images of specific natural landscape features for the purpose of qualifying images that create a visual relaxation tool as illustrated and described in the embodiments herein.

Disclosed in embodiments herein is a method for eliciting a relaxation response, the method comprising: obtaining, using a computing device, a plurality of images; selecting a subset of images, from said plurality of images, satisfying a plurality of natural landscape selection criteria; calculating, with the computing device, an average fractal dimension for each of the images in the subset over a range of thresholds; retaining, within memory accessible by a relaxation response display device, each of the images from the subset having a calculated average fractal dimension within a pre-determined range; and providing the retained images in a serially arranged sequence, and displaying said sequence of images on a relaxation response display device.

Also disclosed in embodiments herein is an apparatus including at least one processor configured to execute programmed instructions stored in memory for calculating an average fractal dimension of an image qualified to elicit a relaxation response from a viewer, comprising: a) thresholding the image (i.e. transforming the image into black and white by applying a threshold against which an actual image intensity value is compared and thereby assigning chosen intensity bounds to be black/white) at a threshold (T) to create a thresholded image; b) covering at least a portion of the thresholded image with boxes; c) counting a number of boxes needed to cover the black/white interface in the thresholded image; d) plotting, a graph for the image with a horizontal (x) axis for the graph being a logarithmic representation of the box size and a vertical (y) axis for the graph being a logarithmic representation of the number of boxes needed to cover the black/white interface in the thresholded image; e) determining a slope of a graphed function relating box size and box count for the thresholded image, which is the fractal dimension for the image at the threshold (T); f) storing the fractal dimension for the thresholded image; g) repeating (a)-(f) for a plurality of thresholds over a range of thresholds; and h) calculating an average of the calculated fractal dimensions for the image based upon the plurality of thresholded images created within the range of thresholds.

Further disclosed in embodiments herein is a relaxation response apparatus, comprising: at least one processor; a memory, coupled to the at least one processor which is configured to execute programmed instructions stored in the memory including: obtaining a plurality of images; selecting a subset of images from the plurality of images which satisfy a plurality of natural landscape selection criteria; calculating a fractal dimension for each of the images in the subset of images; retaining for display only those images from the subset having a calculated average fractal dimension within a predetermined range; storing the retained images in memory in a sequence; and a display for displaying the retained images in the sequence.

BRIEF DESCRIPTION OF THE DRAWINGS

The accompanying figures, in which like reference numerals refer to similar elements throughout the separate views and which are incorporated in and form a part of the specification, further illustrate the embodiments and, together with the detailed description, serve to explain the embodiments disclosed herein. The drawings are for purposes of illustrating various embodiments and are not to be construed as limiting, wherein.

The various embodiments described herein are not intended to limit the disclosure to those embodiments described. On the contrary, the intent is to cover all alternatives, modifications and equivalents as may be included within the spirit and scope of the disclosure.

DETAILED DESCRIPTION

Figure 3:
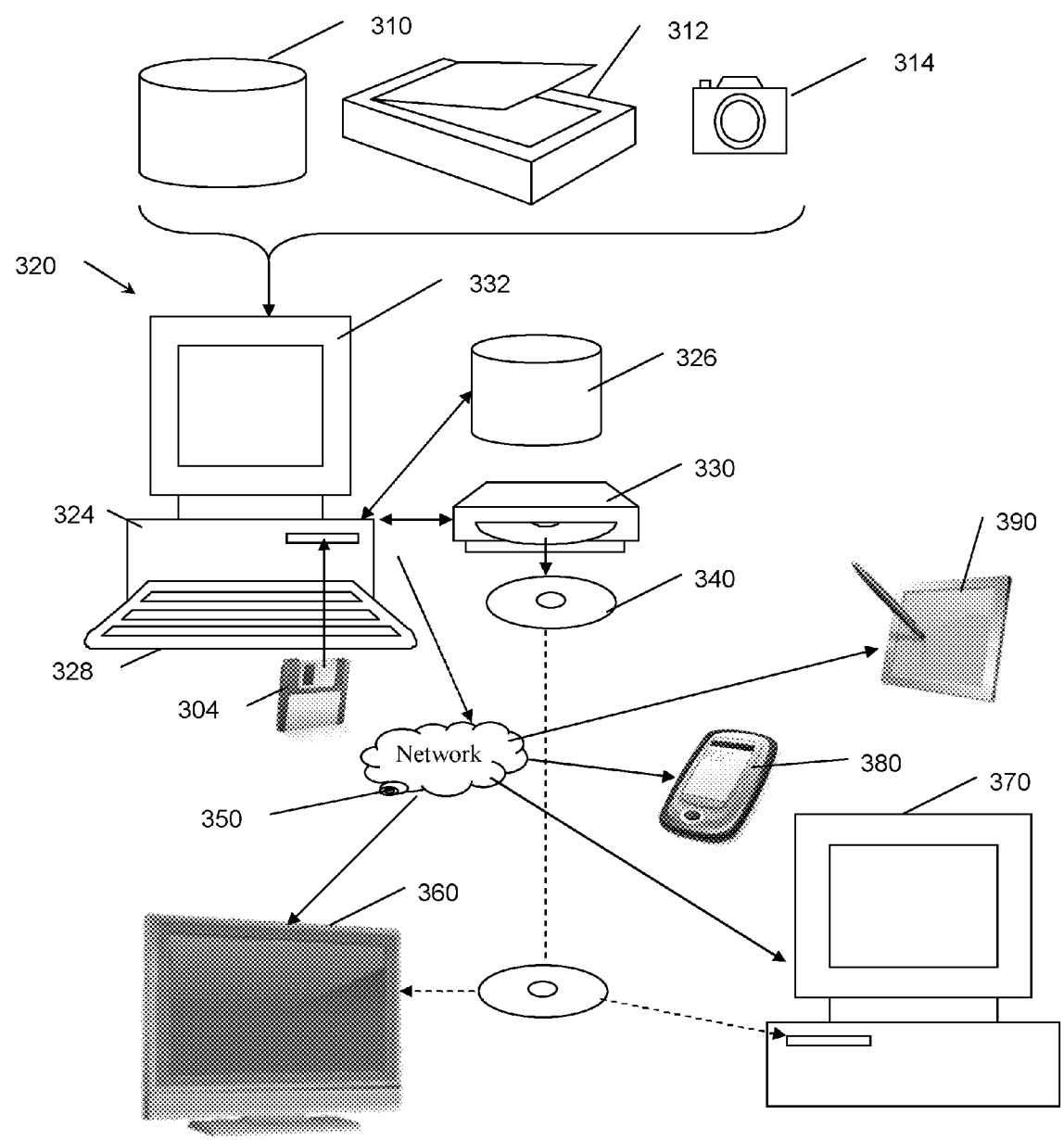
FIG. 3 is a diagram illustrating various embodiments for implementation of the system and methods disclosed.

The following disclosure is directed to exemplary methods, devices, and non-transitory (in time) computer readable media with programmed instructions that result in the selection of images to elicit a relaxation response based on pictorial content and mathematical characteristics. Referring briefly to FIG. 3, depicted therein is a relaxation response computing device 320 including a processor or central processing unit (CPU) 324, memory 326, a user input device(s) 328 (e.g., mouse, keyboard, touch-screen, stylus, etc.), a display device 332, and an interface system that are coupled together by a bus, link or similar communications channel, which may include wireless communications channels. It will be further appreciated that system 320 may include multiple and other types of components, parts, devices, systems, and elements in various configurations and locations.

The processor 324 in the relaxation response computing device executes a program of stored instructions on any non-transitory computer readable medium 304, which may include one or more aspects of the embodiments herein, although the processor could execute other numbers and types of programmed instructions. The memory 326 in the relaxation response computing device stores these programmed instructions and images for one or more aspects of the present invention as described and illustrated herein, although some or all of the programmed instructions could be stored and/or executed elsewhere. A variety of different types of memory storage devices, such as a random access memory (RAM), a read only memory (ROM) or a floppy disk, hard disk, CD, DVD, flash drive, or other computer readable medium which is read from and/or written to by a magnetic, optical, or other reading and/or writing system that is coupled to the processor in the system 320, can be used for the memory.

The user input in the relaxation response computing device is used to input information such as information relating to image selection and presentation, as well as viewing the final output or product of the disclosed process (e.g., a sequence of qualified images eliciting a relaxation response). The user input device 328 can include keypads, a mouse, touch screens, and/or vocal input processing systems although other types and numbers of user input devices can be used.

The display device 332, within the system 320 or as part of a separate display system 360, 370 or 380, is used to show the digital images selected to elicit the relaxation response to a user or viewer. The display unit is, in one embodiment, a computer display, although most any display unit is acceptable so long as it is capable of displaying the images or a movie made from the images in a conventional manner without distortion.

The network interface is used to operatively couple and communicate between relaxation response computing device or system 320 and other devices via one or more communication networks 350. By way of example only, the one or more communication networks 350 can use TCP/IP, and other industry-standard protocols, including HTTP, HTTPS, WAP, and SOAP, as well as wireless communications networks, cellular communications networks, 3G/4 G communications networks, Public Switched Telephone Network Packet Data Networks, the Internet, intranets, e-mail and combinations thereof, each of which may have their own communications protocols.

Although an example of the relaxation response computing device is described herein, this technology can be implemented on any suitable computer system, workstation or other type of computing device, including portable and wireless devices such as a Personal Digital Assistant (PDA), a smartphone (e.g., iPhone) 380, a tablet (e.g. iPad) 390, etc. It is to be understood that the devices and systems of the embodiments described herein are for exemplary purposes, as many variations of the specific hardware and software used to implement the embodiments are possible, as will be appreciated by those skilled in the relevant art. Furthermore, each of the systems of the embodiments may be conveniently implemented using one or more general purpose computer systems, microprocessors, digital signal processors, and micro-controllers, programmed according to the teachings of the embodiments, as described and illustrated herein, and as will be appreciated by those of ordinary skill in the art.

At least one of the disclosed embodiments contemplates the production of an application, including a set of qualified images or a movie produced, and stored on a non-transitory computer readable medium. In the case of an application, the medium may further include instructions stored thereon for one or more aspects of the disclosed methods, which when executed by a processor, cause the processor to carry out the steps necessary to implement the methods and to provide a serial display of evidence based visual elements that evoke psychological and physiological stress reduction by viewers.

Having described an exemplary system for carrying out aspects of the disclosed embodiments, attention is turned to the method for qualifying images that will elicit a relaxation response. As set forth below and depicted in FIGS. 1-2, the aforementioned relaxation response from visual stimuli has been shown to be optimized in response to certain image characteristics. In one embodiment, the characteristics of the image are separated into those that may be described as general image content—the content of the scene, and those that may be characterized in a more quantitative sense using a fractal analysis. Although natural images with evidence-based content may be suitable for a positive relaxation response, the selection of images likely to be most effective at eliciting such a response from a broad audience requires specific characteristics that combine content criteria as well as fractal analysis. One method to elicit a relaxation response is the qualification or selection of images in accordance with the method illustrated by FIG. 1.

The method starts by selecting a digital image from a collection of images 150, such as may be stored on a storage medium, network, etc. As illustrated in FIG. 3, the source of potential images may be pre-existing images stored on a disk 310 (including a networked data source), a scanner 312 suitable for scanning photographs and creating digital representations thereof, as well as a digital camera 314 or other known and future sources of images. Whatever the source of possible images to be qualified, an image is first selected at step 152 for analysis. It will be appreciated that the images may be of various file formats and that they may be converted during processing to utilize a common image format, resolution, etc. The qualification operation represented by step 154 is intended to analyze both image content and the average fractal dimension of the image as will be described in more detail relative to FIG. 2. However, if the image is qualified, it is saved by the system in memory, possibly in a work folder as represented by operation 132. The general image qualification process then continues at step 160, where a test is conducted to determine if more images are available for analysis. If so, the next image is selected at 152 and the process repeated. If not, the image qualification operation is complete, and processing continues at 134 on those images that were identified as being qualified.

Figure 1:
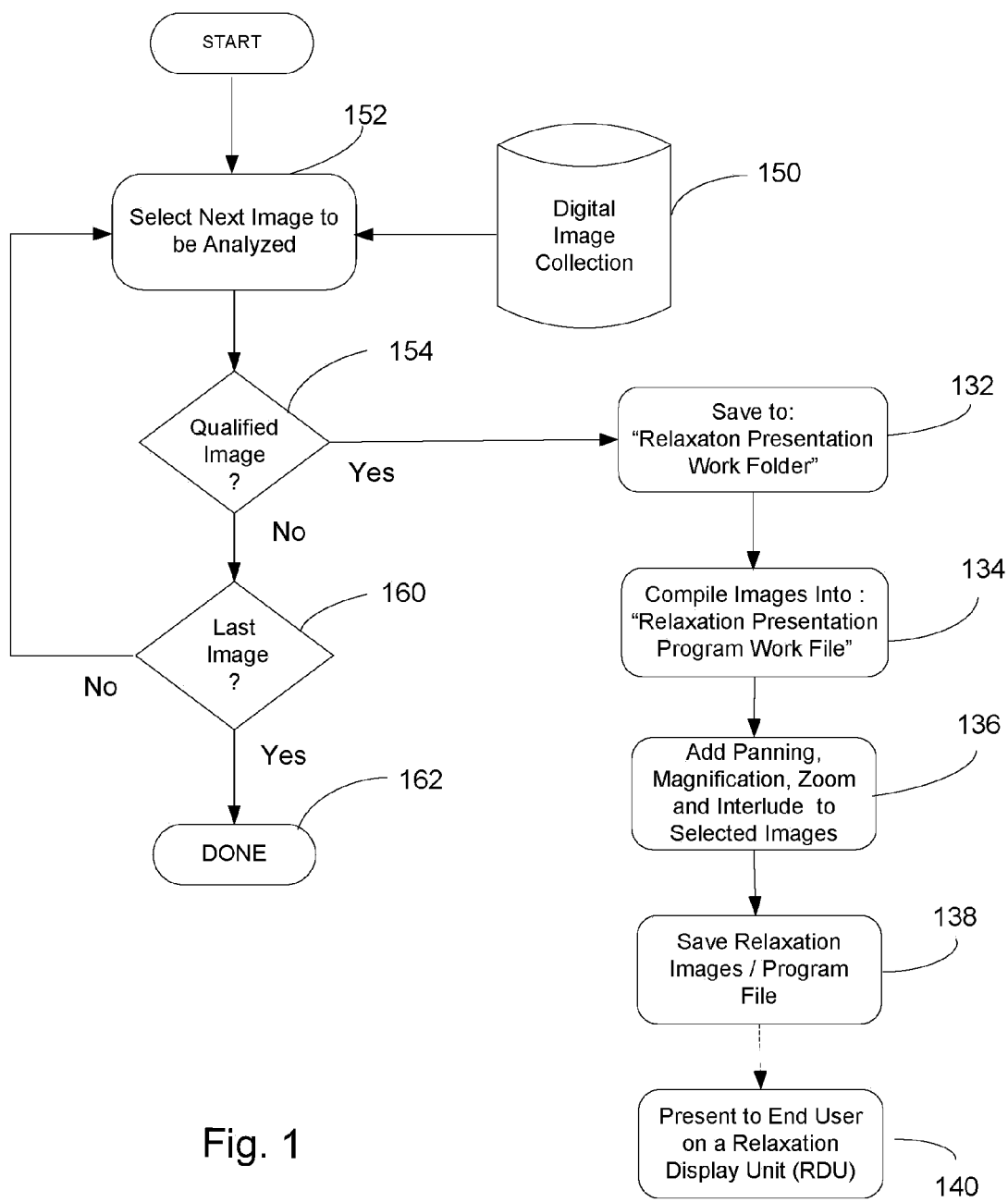
FIG. 1 is a general flowchart of a method for qualifying images that will elicit a relaxation response.

As illustrated in operations 134-138 of FIG. 1, and optionally 140, the images that are qualified are stored in a work file or memory region where they may be compiled into a sequence of images that are displayed under the programmatic control of another application (e.g., a slideshow), or are compiled into a movie or similarly displayable rendition. The compilation of the sequence of images is represented by operation 134, and it is further contemplated that certain images may be identified to add panning, zooming or other display techniques so as to "interest" a viewer and avoid the simple display of one image after another. More specifically, dynamic graphic attributes may be applied to certain still images through the use of panning and zooming effects such as those employed by documentary photographer Ken Burns, for example. Images that are considered suitable for panning typically have a perspective whereby the viewer's attention is retained by panning across the image to a selected area and then zooming in on the specific subject, such as a sunset or mountain top. Also contemplated is starting with a particular portion of a scene in the displayed frame and zooming out to show surrounding area. In other words the viewer is drawn into the scene by accentuating specific areas of selected images. In addition, an interlude between images is possible to provide for a "soft" transition between images, such as a fade in and out, wipe, dissolve and the like. In general, the sequencing of the images will result in each image being displayed for viewing over a time in the range of approximately 15-18 seconds, although time periods of as little as 4 seconds may be adequate to elicit the desired relaxation response.

Once edited, the images may be compiled into a set of images and/or a movie and saved as indicated by operation 138, where they are then "packaged" in optional step 140 as a medium best suited for the subsequent viewing by a user or users. As described above relative to FIG. 3, there are various display devices and technologies that may be employed for displaying the images or movie. The fundamental requirement for a suitable display is that it includes a means for presenting the images that are provided to the display device—for example on a portable storage medium 340, or network 350. The potential display devices are varied and include a flat screen display 360, computer monitor 370, smart phone 380, as well as a variety of alternative display devices such as laptop computers, notepads, televisions (including closed-circuit devices) and so forth.

Also contemplated herein is the use of new media distribution technologies that enable access to the images/movie generated as part of operation 138 in FIG. 1. In one embodiment it is contemplated that optically read codes, such as quick response codes, (QR) may be employed in various publications, syndicated and otherwise, to direct a user to a website or other on-line resource where an example or demo image can be automatically downloaded for display or viewing via an Internet browser. It is also contemplated that images may be sent or distributed to users on a regular basis, based upon a subscription scenario, where users or organizations wishing to use the images may receive periodic updates of images (e.g., monthly) based upon a paid subscription. Such a distribution method contemplates both digital download and or distribution via a CD or DVD. It is also possible that the images could be updated periodically and that an application (app) running on a handheld computing device or PDA would automatically receive and update the images/movie displayed.

Also contemplated as part of the distribution of images/movies is the possibility of providing the image qualification software as a licensed application on a computer medium, such that users may independently operate a program to qualify images that they have access to for their own use. In other words, a person who has access to a number of images may be able to execute the qualification operation (154) on images that they own, and use them alone or in combination with pre-qualified images, and thus be able to elicit the desired response while employing images that may be more familiar or recognizable (e.g., a serene setting on a lake where the user has camped for many years).

Figure 2:
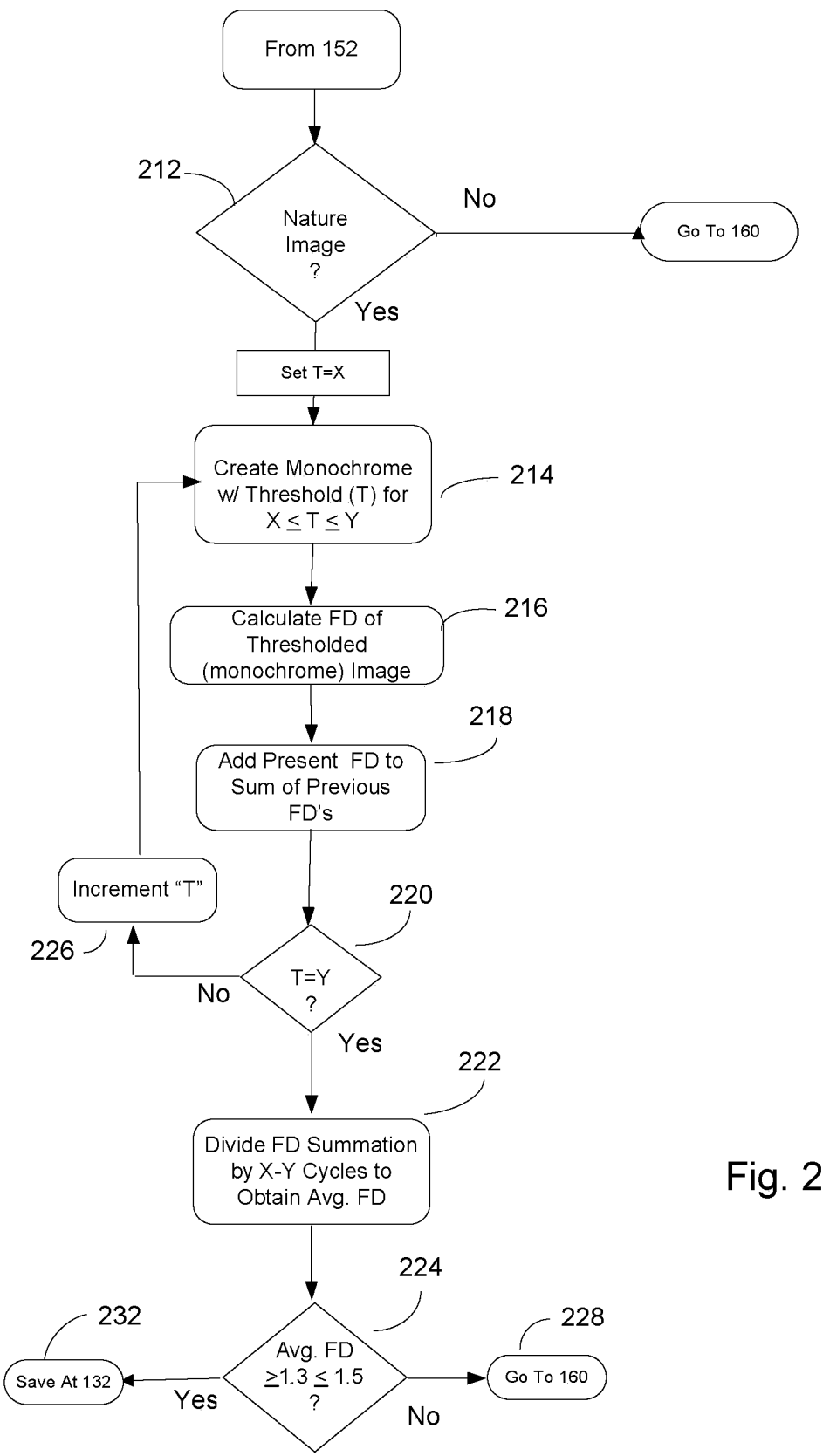
FIG. 2 is a detailed flowchart illustrating a method for qualifying images in accordance with one embodiment.

Having described the operations set forth in FIG. 1, attention is turned to FIG. 2, where more specific information is provided relative to a methodology used for qualification of images in accordance with the disclosed embodiments. The process of FIG. 2 begins by selecting a subset of images from the plurality of images to be analyzed by identifying those images that satisfy a criteria that the content of the image include natural landscape elements. The criteria for select elements include the following:

(i) low growth (bushes, grasses, flowers), perhaps suggestive of a food source;

(ii) open areas, indicative of ease of egress/movement;

(iii) trees, for shelter or safety;

(iv) sky (v) horizon visible, for judgment of depth;

(vi) no man-made artifacts or structures;

(vii) water may be included in the scenes—must be fresh water;

(viii) people or creatures may be included sparingly in the scenes and must appear docile, content and at ease; and (ix) creatures must not be those that are generally aggressive to humans Selection of the desirable images should include those that exhibit some or all elements set forth in criteria (i)-(vi) above. Criteria (vii)-(ix) are then used to further qualify images and to eliminate those that are less likely to elicit the desired relaxation response.

As indicated by operation 212, the content of each image is identified and compared to the list of elements above. Images including content not listed are excluded ("No" response in 212) and are not used. In the event that the image includes elements described above as depicting a natural scene, a "Yes" response is generated from operation 212. It will be appreciated that various methods may be employed to characterize the images for the operation in 212. One embodiment contemplates the use of search tools to collect images that are pre-identified as including such elements. For example, an on-line collection of photographs may include descriptive information about such photos, permitting a pre-screening for desirable elements. It is also contemplated that image analysis software or similar tools may be employed to execute the operation of step 212 and select images meeting the criteria of nature or natural scene. Human interaction in the selection process may also be employed so as to assure the application of the criteria indicated above.

Once the image has been indicated to meet the requirement of the first criteria or characteristic, further analysis proceeds to determine an average fractal dimension for the image across a range of thresholds. Fractals are irregular geometric shapes that may be reduced or subdivided into parts, each of which is a reflection (partial self-similarity) of the whole in ever decreasing size. The fractal dimension is represented as a logarithmic number between 1 and 2, (having no actual dimensional units), which quantifies the irregular, complex image, much as the length and width would describe a rectangle. This geometrical complexity characterized by a fractal quantity is frequently experienced when dealing with natural objects such as coastlines, mountains, trees and so forth. One of the methods commonly used to mathematically quantify fractal shapes in images is referred to as "box counting." This technique involves covering a black/white interface in a two-dimensional black and white fractal image with square boxes and counting how many boxes are needed to cover the selected fractal. This is repeated numerous times with boxes of different sizes. This box counting process ultimately results in data that may be characterized using a graphical function with a horizontal (x) axis being a logarithmic representation of the box size and a vertical (y) axis representing a logarithmic representation of the number of boxes needed to cover the fractal image or the image section of interest. The slope of the function of the graph is further considered an approximation of the image's fractal dimension. It is slope of the black-white interface region that defines the outline of the shapes within an image and is utilized as the region for determination of the box count and slope that define the fractal dimension for the particular image.

Fractal dimensions quantify the self-similarity or scaled similarity that is present in nature, for example the limb of a tree very closely resembles the tree itself and a branch resembles a limb, a twig a branch and so on. Although a limb is not an exact duplicate of the tree, it does look similar. A fractal dimension (D) is a way to describe the micro-transitions within a region of self-similarity in a picture—residing somewhere between "smooth to rough" (i.e. less complex to more complex) as expressed in the following equation; $D=\log[(N)(r)/\log(1/r)]$, where N=the number of boxes to cover the image edge and r=the number of pixels within the perimeter or area of the box (i.e., box size).

In the case where an image is qualified as a natural scene and has an average fractal dimension within a desirable range it is suitable to elicit a relaxation response. Further considering FIG. 2, in view of FIG. 1, the average fractal dimension for an image is obtained using an iterative process set forth in operations 214-220 and 226. Initially, using a threshold (T) the image is thresholded to create a thresholded or monochrome image at 214. To determine the fractal dimension at that threshold 216, in one embodiment the thresholded image is covered with boxes, and the number of boxes needed to cover the thresholded image's black/white interface are counted. The boxes are then characterized as a function, possibly by plotting, a graph for the image with an x-axis for the graph being a box size and a y-axis for the graph being a number of boxes needed to cover the thresholded image's black/white interface, and then determining the slope of the graphed function relating box size and box count for the black/white interface of the thresholded image. The slope of the function may be characterized as the fractal dimension for the thresholded image and produced as an output of operation 216. The fractal dimension for the thresholded image is then stored, and summed with the fractal dimension calculated for subsequent threshold levels as represented in 218. This process is repeated or iterated for a plurality of thresholds as represented by operations 220 and 226.

As will be appreciated the thresholds may be incremented by a fixed amount for each of the iterations, which will likely result in incremental changes to the thresholded image that is analyzed each time the fractal dimension is calculated. The disclosed embodiment contemplates execution of programmed instructions stored in a computer memory for first thresholding the image and creating a black and white thresholded image based on a threshold intensity value (T), such that part of the image is converted to white for those pixels equal to or above the threshold and converted to black for those pixels below the threshold. A computer processor, such as processor 324 in FIG. 3, may be configured to execute instructions stored in memory to convert each image to a black and white thresholded image using each of a plurality of threshold values (T) over the range of $X<=T<=Y$, and both calculating a fractal dimension for each of the selected images as well as summing the fractal dimensions calculated. The use of a range of thresholds is intended to provide an accurate characterization of an image's average fractal dimension even though there is no standardization or normalization between images.

In one embodiment the value of X is a threshold value where all pixels in the image are represented as white when T equals X and less, and Y is a threshold value where all pixels in the image are represented as black when T equals Y and greater. In an alternative embodiment, the value of X is a threshold where structure in the image is represented as black on a white background when T equals X and less, and Y is a threshold value where structure in the image is represented as white on a black background when T equals Y and greater.

Various techniques may be employed to calculate the fractal dimension for a thresholded image, or a series of thresholded images covering a range of thresholds. One such technique employs an on-line or application software carried out on a computer or processor (e.g., HarFa 5.4L freeware; Harmonic and Fractal Image Analyzer, available from the Institute of Physical and Applied Chemistry, Brno University of Technology, Brno, Purkynova 118, 612 00, Czech Republic.) As indicated above, the average fractal dimension is calculated for an image over the range of thresholds X to Y, and the average is obtained at operation 222. The average fractal dimension is then compared to a range of acceptable fractal dimensions (e.g., the range of 1.3 to 1.5) as indicated at test 224. If the average fractal dimension (FD) is greater than or equal to 1.3 and less than or equal to 1.5, then the image is qualified and is added to the work folder at operation 132 in FIG. 1.

Figure 4:
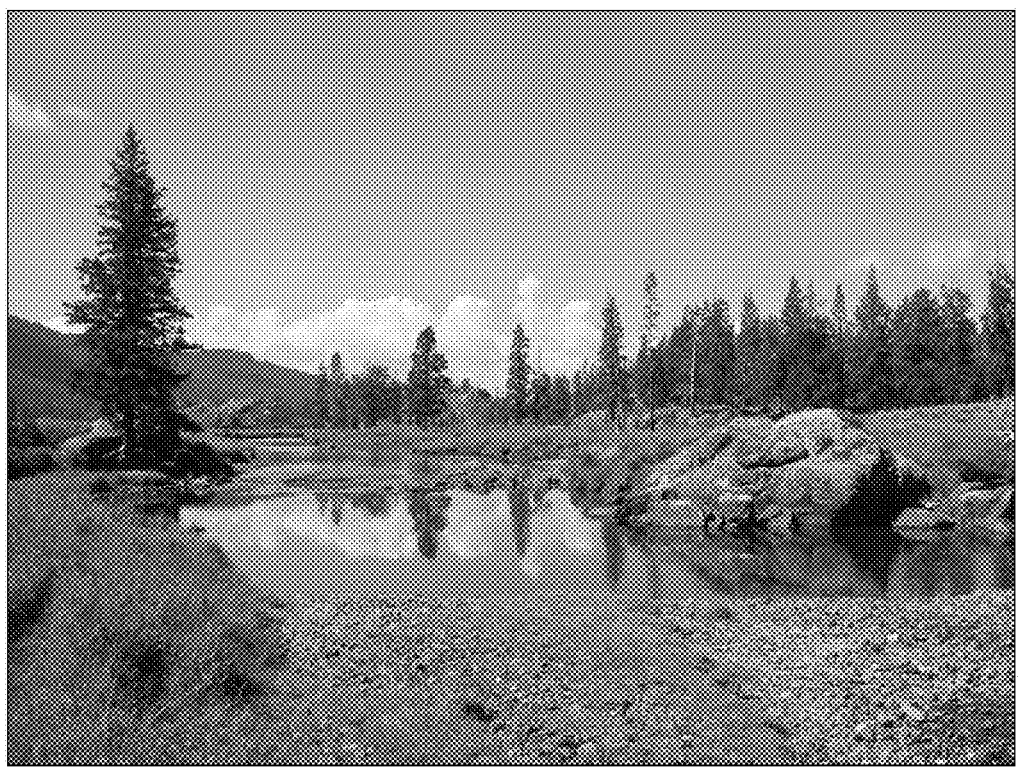
FIG. 4 is a grayscale representation of an exemplary natural landscape scene.
Figure 5:
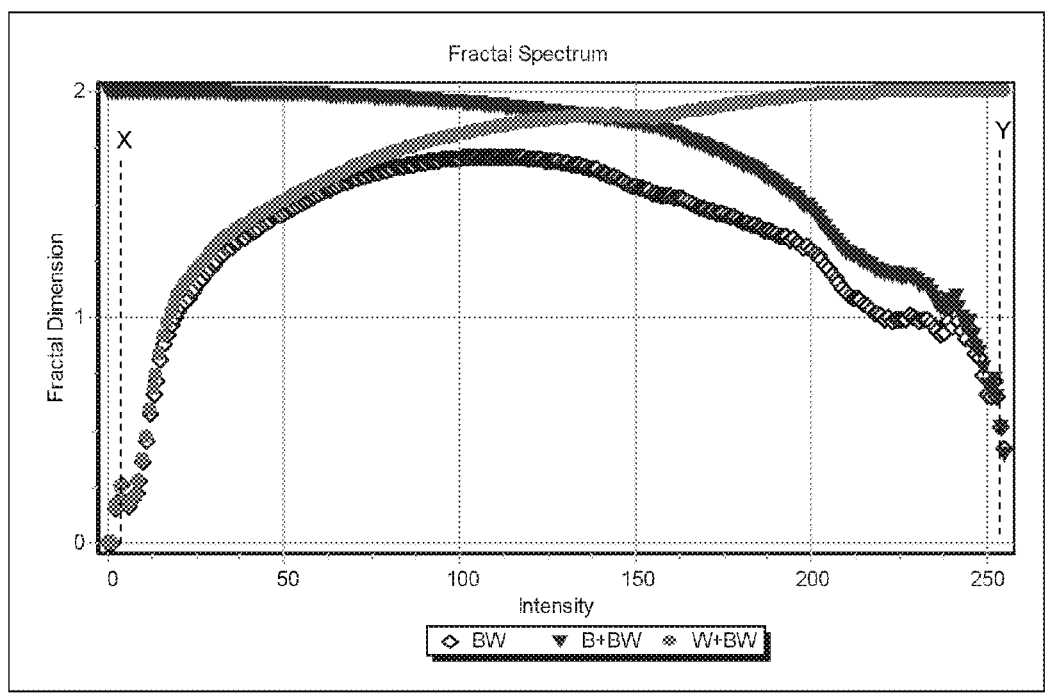
FIG. 5 is a graph illustrating the fractal dimensions obtained for various thresholds applied to the image of FIG. 4.
Figure 6:
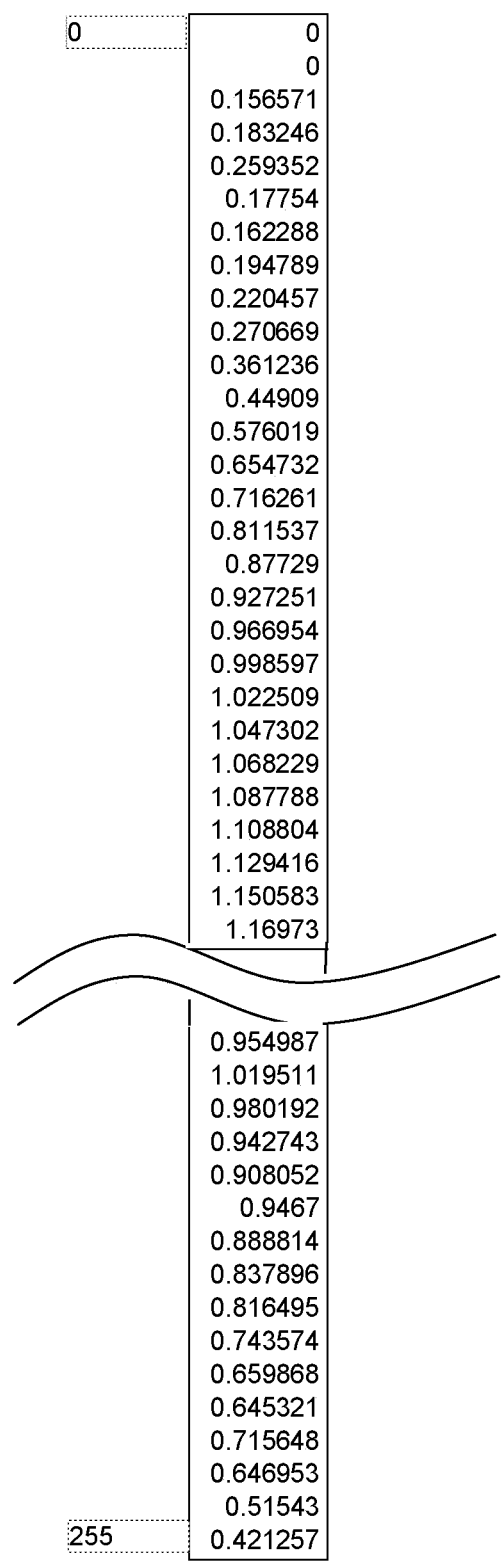
FIG. 6 is a partial table listing calculated fractal dimensions over a range of thresholds applied to the image of FIG. 4.

FIGS. 4-6 provide an exemplary illustration of the characteristics of an image that would be selected by the disclosed methods. FIG. 4 is an exemplary image (shown in single-color for purposes of the patent, but could also be a color image) showing aspects of a natural landscape scene. For example, FIG. 4 includes low growth bushes and grasses, open area, trees and a sky/horizon for judgment of depth. Moreover, there are no man-made artifacts or structures. The image would, therefore, be classified as a natural landscape. FIG. 5 illustrates, in a graphical form, the fractal dimensions obtained over a range of thresholds applied to the image of FIG. 4. As the graph illustrates, the black/white interface threshold is calculated over the range of thresholds X to Y, for example, 5 to 252. As indicated above, in some images the thresholds applied at very low or very high intensity levels does not result in discernible structure within the thresholded image, and thus results in zero or other outlier values for the fractal dimension. Once the images are processed, to produce a plurality of thresholded images for various threshold intensities (T) over the range, then the fractal dimension is calculated for each T and averaged. Like the graph of FIG. 5, the table shown in FIG. 6 is illustrative of the fractal dimension data obtained for the image of FIG. 4, although only a portion of the data is illustrated in the figure. The average fractal dimension may then be compared to determine if it is within a range of acceptable fractal dimensions as described above. If the average fractal dimension (Avg. FD) is within the range then the image is qualified and is added to the work folder at operation 132 in FIG. 1.

As discussed, fractal dimensions are obtained by using the box counting method which first requires the creation of black and white fractal structures using a process referred to as "thresholding". This image processing technique transforms grayscale and/or color images into black (binary 0) or white (binary 1) pixels. The actual threshold point(s) can be changed to produce differently-appearing fractal structures. Accordingly, the disclosed method employs a plurality of thresholds over a range. Accordingly, various fractal dimensions are achieved for any single image depending upon the threshold point. In order to better characterize an image by its fractal dimension an average of a range of thresholds is used. This average fractal dimension (Avg. FD) now represents a non-dimensional logarithmic value that characterizes the average fractal dimension for the image on a scale between 1 and 2.

Also contemplated is the creation of a series or sequence of visual images, selected and analyzed in accordance with the methodology described herein, so that each image in the sequence encompasses both evidence-based content from nature, as well as evidence-based mathematical characteristics (e.g., an average fractal dimension with a defined range), where the images are saved on storage media for viewing and evoking stress reduction (the relaxation response) and reduction in sequelae of stress.

Once the series of evidence-based and content-complexity qualified images is created and saved, completing operations 132-138 of FIG. 1, it is expected that an end user would utilize the image series by loading and displaying the production on any or all of several currently available devices. By way of example only, the product could be displayed on a computer monitor of a computing device (via DVD, CD, direct download, or transfer from an external memory source to which the series was downloaded), on a television (currently via DVD technology), on a digital picture frame (via transfer from an external memory source such as a DVD, flash drive, or memory card to which the series was downloaded), or on a portable display such as a PDA or video/music player (via download to internal memory), although other types of display devices could be used. During viewing of the series on the display device an optimized or otherwise desired relaxation response is elicited from the end user transforming the end user to a calmer state. Accordingly, one of the advantages of this technology is that it analyses and identifies both the content and a mathematical quality of an image so as to identify images which have the greatest potential to visually elicit a relaxation response that is desired or optimized.

Although an example of the relaxation response compiling device is described herein, the disclosed embodiments may be implemented on any suitable computer system or other type of computing device. It is to be understood that the devices and systems of the embodiments described herein are for exemplary purposes, as many variations of the specific hardware and software used to implement the embodiments are possible, as will be appreciated by those skilled in the relevant art. Furthermore, each of the systems of the embodiments may be implemented using one or more general purpose computer systems, microprocessors, and micro-controllers, programmed according to the teachings of the embodiments, as described and illustrated herein, and as will be appreciated by those of ordinary skill in the art. Also, various presently unforeseen or unanticipated alternatives, modifications, variations or improvements therein may be subsequently made by those skilled in the art which are also intended to be encompassed by the disclosure and following claims.

What is claimed is:

1. A method for eliciting a relaxation response, the method comprising:
   obtaining, using a computing device, a plurality of images;
   selecting a subset of images, from said plurality of images, satisfying a plurality of natural landscape selection criteria;
   calculating, with the computing device, an average fractal dimension for each of the images in the subset, where the average fractal dimension is an average of fractal dimensions determined for each image when a plurality of thresholds are applied to each image over a range of thresholds;

retaining, within memory accessible by a relaxation response display device, each of the images from the subset having a calculated average fractal dimension within a pre-determined range; and providing the retained images in a serially arranged sequence, and displaying said sequence of images on a relaxation response display device.

2. The method as set forth in claim 1 wherein the natural landscape selection criteria comprises an image that illustrates at least one low growth feature selected from the group consisting of low growth bushes; low growth grasses, low growth flowers, and in addition an open area, trees, a horizon, a visible sky, fresh water, when water is included, and an absence of man-made structures.

3. The method as set forth in claim 1 wherein calculating an average fractal dimension for each of the images further comprises:
a) thresholding the image at a threshold (T) to create a thresholded image with black/white interface;
b) covering at least a portion of the thresholded image with boxes;
c) counting how many boxes are needed to cover all of the black/white interface in the thresholded image;
d) plotting a graph for the image with a horizontal axis for the graph being a logarithmic representation of box size for the boxes and a vertical axis for the graph being a logarithmic representation of how many boxes are needed to cover all black/white interface in the thresholded image; and
e) determining a slope of a graphed function relating box size and box count for the thresholded image, which is the fractal dimension for the image at the threshold (T),
f) storing the fractal dimension for the thresholded image;
g) repeating (a)-(f) for a plurality of thresholds over the range of thresholds; and
h) calculating an average of the calculated fractal dimensions for the image based upon the fractal dimension stored for a plurality of thresholds over the range of thresholds.

4. The method as set forth in claim 3, wherein (a)-(f) are repeated for each of a plurality of thresholds over the range of thresholds, where the average of the calculated fractal dimensions for the image is based upon thresholded images for each of the plurality of thresholds over the range of thresholds.

5. The method as set forth in claim 1 wherein the predetermined range for the average fractal dimension is between 1.3 and 1.5.

6. The method as set forth in claim 1 wherein displaying of the retained images further comprises compiling a sequence of images wherein the sequence of images has dynamic graphic attributes applied to at least one image in the sequence when compiling, including altering image magnification while displaying the at least one and fewer than all of the retained images in the sequence of images.

7. A non-transitory computer readable medium having stored thereon a plurality of images and associated commands for eliciting a relaxation response comprising machine executable code, which, when executed and viewed on a display causes the display of relaxation images to an individual, said relaxation images all including qualifying natural landscape content and qualifying average fractal dimension in the range of 1.3 to 1.5, where the average fractal dimension is determined for each image from fractal dimensions calculated when each of a plurality of thresholds are applied to each image over a range of thresholds.

8. The medium as set forth in claim 7, wherein the relaxation images further include a compilation of a sequence of images wherein the sequence of images has dynamic graphic attributes applied to at least one image in the sequence, including altering the display of at least one of the relaxation images in the sequence of images by applying an alteration selected from the group consisting of panning and zooming.

9. An apparatus including at least one processor configured to execute programmed instructions, stored in memory for calculating an average fractal dimension of an image qualified to elicit a relaxation response from a viewer, the programmed instructions comprising:
a) thresholding the image at a threshold (T) to create a thresholded image with black/white interface;
b) covering at least a portion of the thresholded image with boxes;
c) counting how many boxes are needed to cover all black/white interface in the thresholded image;
d) plotting a graph for the thresholded image with a horizontal axis for the graph being a logarithmic representation of box size for the boxes and a vertical axis for the graph being a logarithmic representation of how many boxes are needed to cover the black/white interface in the thresholded image;
e) determining a slope of a graphed function relating box size and box count for the thresholded image, which is the fractal dimension for the image at the threshold (T);
f) storing the fractal dimension for the thresholded image;
g) repeating (a)-(f) for a plurality of thresholds over a range of thresholds; and
h) calculating an average of the calculated fractal dimensions for the image based upon the thresholded image created over the range of thresholds, where the average fractal dimension is an average of the stored fractal dimension for each of the plurality of thresholds over the range of thresholds.

10. The apparatus as set forth in claim 9 wherein the processor is further configured to execute programmed instructions stored in the memory for thresholding the image, further comprising converting the image from a color image to a black and white thresholded image based on a threshold intensity value such that part of the image is converted to white for pixels having an intensity equal to or above the threshold and converted to black for pixels having an intensity below the threshold.

11. The apparatus as set forth in claim 9 wherein the processor is further configured to execute programmed instructions stored in the memory further comprising:
converting each image of a collection of images to a black and white thresholded image using each of a plurality of threshold values over the range; and
calculating an average fractal dimension over the range for each image in the collection of images.

12. The apparatus as set forth in claim 11 wherein the range for an average fractal dimension is between 1.3 and 1.5, and is used to qualify each image of the collection of images as one that will elicit a relaxation response.

13. The apparatus as set forth in claim 9, where the image is qualified to elicit a relaxation response and is stored as a retained image, wherein the processor is further configured to execute programmed instructions stored in the memory for altering a display of at least one retained image in a serially arranged sequence.

14. The apparatus as set forth in claim 9 wherein the processor is further configured to execute programmed instructions stored in the memory for applying a zoom to at least one image qualified to elicit a relaxation response.

15. An apparatus including at least one processor configured to execute programmed instructions stored in memory for calculating an average fractal dimension of an image qualified to elicit a relaxation response from a viewer, wherein the processor is further configured to execute programmed instructions stored in the memory comprising:
   a) thresholding the image at a threshold (T) to create a thresholded image with black/white interface, including converting the image to a black and white thresholded image using each of a plurality of threshold values over a range of X<=T<=Y, wherein the value of X is a threshold value where all pixels in the image are represented as white when T equals X and less, and Y is a threshold value where all pixels in the image are represented as black when T equals Y and greater; and
   calculating a fractal dimension for the thresholded image, and further comprising:
   b) covering at least a portion of the thresholded image with boxes;
   c) counting how many boxes are needed to cover all black/white interface in the thresholded image;
   d) plotting a graph for the thresholded image with a horizontal axis for the graph being a logarithmic representation of box size for the boxes and a vertical axis for the graph being a logarithmic representation of how many boxes are needed to cover the black/white interface in the thresholded image;
   e) determining a slope of a graphed function relating box size and box count for the thresholded image, which is the fractal dimension for the image at the threshold (T);
   f) storing the fractal dimension for the thresholded image at the threshold (T);
   g) repeating (a)-(f) for each of the plurality of threshold values over the range; and
   h) calculating an average of the stored fractal dimension for each of the plurality of threshold values over the range.

16. An apparatus including at least one processor configured to execute programmed instructions stored in memory for calculating an average fractal dimension of an image qualified to elicit a relaxation response from a viewer, wherein the processor is further configured to execute programmed instructions stored in the memory comprising:
   a) thresholding the image at a threshold (T) to create a thresholded image with black/white interface, including converting the image to a black and white thresholded image using each of a plurality of threshold values over a range of X<=T<=Y, wherein the value of X is a threshold where structure in the image is represented as black on a white background when T equals X and less, and Y is a threshold value where structure in the image is represented as white on a black background when T equals Y and greater; and
   calculating a fractal dimension for the thresholded image, and further comprising:
   b) covering at least a portion of the thresholded image with boxes;
   c) counting how many boxes are needed to cover all black/white interface in the thresholded image;
   d) plotting a graph for the thresholded image with a horizontal axis for the graph being a logarithmic representation of box size for the boxes and a vertical axis for the graph being a logarithmic representation of how many boxes are needed to cover the all black/white interface in the thresholded image;
   e) determining a slope of a graphed function relating box size and box count for the thresholded image, which is the fractal dimension for the image at the threshold (T);
   f) storing the fractal dimension for the thresholded image at the threshold (T);
   g) repeating (a)-(f) for the plurality of threshold values over the range; and
   h) calculating an average of the stored fractal dimension for each of the plurality of threshold values over the range.

17. A relaxation response apparatus, comprising:
   at least one processor;
   a memory, coupled to the at least one processor which is configured to execute programmed instructions stored in the memory including:
      obtaining a plurality of images;
      selecting a subset of images from the plurality of images which satisfy a plurality of natural landscape selection criteria;
      calculating an average fractal dimension over a range of thresholds for each of the images in the subset of images, where the average fractal dimension is an average of fractal dimensions determined for each of the images when a plurality of thresholds are applied to each of the images over a range of thresholds;
      retaining for display only those images from the subset having a calculated average fractal dimension within a predetermined range;
      storing the retained images in memory in a sequence; and
   a device for displaying the retained images in the sequence.

18. The apparatus as set forth in claim 17 wherein the plurality of natural landscape selection criteria are selected from the group consisting of:
   low growth bushes;
   low growth grasses;
   low growth flowers;
   an open area;
   trees;
   a horizon;
   a visible sky;
   an absence of any man-made structures; and
   fresh water, when water is included.

19. The apparatus as set forth in claim 17 wherein the at least one processor is further configured to execute programmed instructions stored in the memory for calculating the average fractal dimension of an image qualified to elicit a relaxation response from a viewer, comprising:
   a) thresholding an image in the subset of images at a threshold (T) to create a thresholded image with black/white interface;
   b) covering at least a portion of the thresholded image with boxes;
   c) counting a number of boxes needed to cover all black/white interface in the thresholded image;
   d) plotting a graph for the thresholded image with a horizontal axis for the graph being a logarithmic representation of box size for the boxes and a vertical axis for the graph being a logarithmic representation of the number of boxes needed to cover the thresholded image;
   e) determining a slope of a graphed function relating box size and box count for the thresholded image, which is the fractal dimension for the thresholded image at the threshold (T);
   f) storing the fractal dimension for the thresholded image;

g) repeating (a)-(f) for a plurality of thresholds over the range of thresholds; and h) calculating an average of the stored fractal dimension for each of the plurality of thresholds over the range of thresholds.

20. The apparatus as set forth in claim 17 wherein the at least one processor is further configured to execute programmed instructions stored in the memory for repeatedly thresholding the image in the subset of images over the range of thresholds, further comprising converting the image from a color image to a black and white thresholded image based on a threshold intensity value (T) such that part of the image is converted to white for pixels having an intensity equal to or above the threshold intensity value (T) and converted to black for pixels having an intensity below the threshold intensity value (T).

21. The apparatus as set forth in claim 17 wherein the predetermined range for the fractal dimension is between 1.3 and 1.5.

22. The apparatus as set forth in claim 17 wherein the at least one processor is further configured to execute programmed instructions stored in the memory for altering the display of at least one of the retained images in the sequence.

23. The apparatus as set forth in claim 22 wherein the at least one processor is further configured to execute programmed instructions stored in the memory for applying an alteration, selected from the group consisting of panning and zooming, to at least one and fewer than all of the retained images.

* * * * *